(12) United States Patent
Michel et al.

(10) Patent No.: US 6,652,746 B2
(45) Date of Patent: Nov. 25, 2003

(54) CHROMATOGRAPHY SYSTEM FOR AUTOMATICALLY SEPARATING DIFFERENT COMPOUNDS IN A SAMPLE

(75) Inventors: Jonathan D. Michel, Charlottesville, VA (US); Robert U. Albrecht, Jr., Crozet, VA (US)

(73) Assignee: Biotage, Inc., Charlottesville, VA (US)

( * ) Notice: Subject to any disclaimer, the term of this patent is extended or adjusted under 35 U.S.C. 154(b) by 0 days.

(21) Appl. No.: 10/108,221

(22) Filed: Mar. 26, 2002

(65) Prior Publication Data

US 2003/0183565 A1 Oct. 2, 2003

(51) Int. Cl.[7] ............................................. B01D 15/08
(52) U.S. Cl. ..................... 210/198.2; 210/143; 210/656
(58) Field of Search ............................... 210/635, 656, 210/659, 143, 198.2

(56) References Cited

U.S. PATENT DOCUMENTS

| | | | | |
|---|---|---|---|---|
| 3,925,207 A | * | 12/1975 | Scriba | 210/198.2 |
| 4,577,492 A | * | 3/1986 | Holba | 210/198.2 |
| 4,724,081 A | * | 2/1988 | Kawahara | 210/198.2 |
| 4,840,730 A | * | 6/1989 | Saxena | 210/198.2 |
| 5,135,658 A | * | 8/1992 | Lee | 210/656 |
| 5,601,707 A | * | 2/1997 | Clay | 210/198.2 |
| 5,670,054 A | | 9/1997 | Kibbey et al. | 210/656 |
| 5,755,559 A | * | 5/1998 | Allington | 210/198.2 |
| 6,080,318 A | | 6/2000 | Gumm et al. | 210/659 |

FOREIGN PATENT DOCUMENTS

| | | | | |
|---|---|---|---|---|
| WO | WO 01/68216 | | 9/2001 | 210/656 |

OTHER PUBLICATIONS

Section from the original Flex release (Dec. 1999) pp. 1–3.
Brochure entitled "Move Into the Flex Lane, The Parallex Flex ™, Flexible Purification System", Biotage, A Division of Dyax Corp., 1999, pp. 1–6.

* cited by examiner

*Primary Examiner*—Ernest G. Therkorn
(74) *Attorney, Agent, or Firm*—Fish & Richardson P.C.

(57) ABSTRACT

A chromatography system including a chromatography column connected to receive a sample and separate different compounds in the sample, a flow-through detector that outputs a signal indicating the presence of compounds in the sample leaving the column, a fraction collector that directs fractions of the sample from the column to separate fraction wells, and an electronic controller that receives inputs from the detector and controls the fraction collector. The electronic controller monitors the signal from the detector over time and initiates a cut from one well to another at the fraction collector when the signal over time experiences a shoulder where the slope of the signal over time does not change in sign but does change by more than a predetermined amount.

20 Claims, 3 Drawing Sheets

CHROMATOGRAPHY SYSTEM FOR AUTOMATICALLY SEPARATING DIFFERENT COMPOUNDS IN A SAMPLE

BACKGROUND

The invention relates to chromatographic separation and fractionation.

A chromatography column can be used to separate different compounds in a sample being flushed through the column in a solvent. The different compounds in the sample are delayed in passage through the column to different extents and exit the column at different times. A fraction collector directs a first part of the sample leaving the column to one fraction-collecting well, the second part to a second well and so on. A detector can be used to detect absorption or another characteristic of the sample during the processing of the sample downstream of the column and upstream of the fraction collector in order to detect the presence of different compounds in the stream from the column and to decide when to begin and terminate collection, and when to advance the fraction collector to a new well.

In a chromatography system available from the Biotage Inc. under the Parallex Flex and Horizon designation, sampling can be initiated and terminated based upon the UV absorbance values or based upon the slopes of these values over time. A fraction cut can be triggered by collected volume (i.e., when a well has been filled to capacity) and by detection of a valley between peaks based upon detection of a change in slope from a negative value to a positive value.

SUMMARY

In one aspect, the invention features, in general, a chromatography system including a chromatography column connected to receive a sample and separate different compounds in the sample, a detector that outputs a signal indicating the presence of compounds in the sample leaving the column, a fraction collector that directs fractions of the sample from the column to separate fraction wells, and an electronic controller that receives inputs from the detector and controls the fraction collector. The electronic controller monitors the signal from the detector over time and initiates a cut from one well to another at the fraction collector when the signal over time experiences a shoulder where the slope of the signal over time does not change in sign but does change by more than a predetermined amount, and the slope is negative.

In another aspect, the invention features, in general, a chromatography system including a chromatography column, a flow-through detector, and a fraction collector as already described. The system also includes an electronic controller that monitors the signal from the detector over time and initiates a cut from one well to another at the fraction collector when the slope is positive and experiences a shoulder as determined by a positive slope at one point in time that is less than a slope threshold, and a positive slope at a later time that is greater than X times the slope threshold, where X is greater than one (preferably greater than 1.5 and most preferably between 1.5 and 2.5).

In another aspect, the invention features, in general, a chromatography system including a chromatography column, a flow-through detector, and a fraction collector. The system also includes an electronic controller that monitors the signal from the detector over time and initiates a cut from one well to another at the fraction collector when the signal is less than a slope detection disable threshold and the signal over time experiences a specified change in slope condition.

In another aspect, the invention features, in general, a chromatography system including a chromatography column, a flow-through detector, and a fraction collector. The system also includes an electronic controller that monitors the signal from the detector over time and identifies valleys in the signal from the detector over time. The system also includes a user interactive display and input device that permits the user to select whether or not to collect during valleys in the signal over time, and the controller either ends collection after identifying a valley or causes a fraction cut at a set time.

In another aspect, the invention features, in general a chromatography system including a chromatography column, a flow-through detector, a fraction collector, and an electronic controller that monitors the signal from the detector over time. The system also includes a user interactive display and input device that permits the user to select to operate in a custom mode in which the user determines setpoint conditions for initiating and ending collection or to operate in one of a set of preset collection modes in which the setpoint conditions for initiating and ending collection are preset.

Preferred embodiments of the invention may include one or more of the following features. In preferred embodiments the electronic controller determines if the signal is in a valley by the slope being positive at a set time delay past the cut when the slope is negative. The controller can cause the fraction collector to move to a new well after the set time delay. Alternately the controller can end collection after the set time delay. The system includes a user interactive display and input device that permits the user to enter the slope threshold, the slope disable detection threshold, the set time delay, and a threshold value for the signal for the controller to initiate and stop collection. The detector emits a signal measuring characteristics of the compound. For example, a UV absorbance detector emits a signal measuring the UV absorbance.

Embodiments of the invention may include one or more of the following advantages. The detection based on UV slope and changes in UV slope allows for more fine tuned control of the fractionation process, leading to higher purity in the chemical compounds collected and higher efficiencies. The user can enter various data to control the stop/start and cut point decision analysis, or can alternatively rely on preselected modes of operation.

Other advantages and features of the invention will be apparent from the following description of a particular embodiment and from the claims.

DETAILED DESCRIPTION

Figure 1:
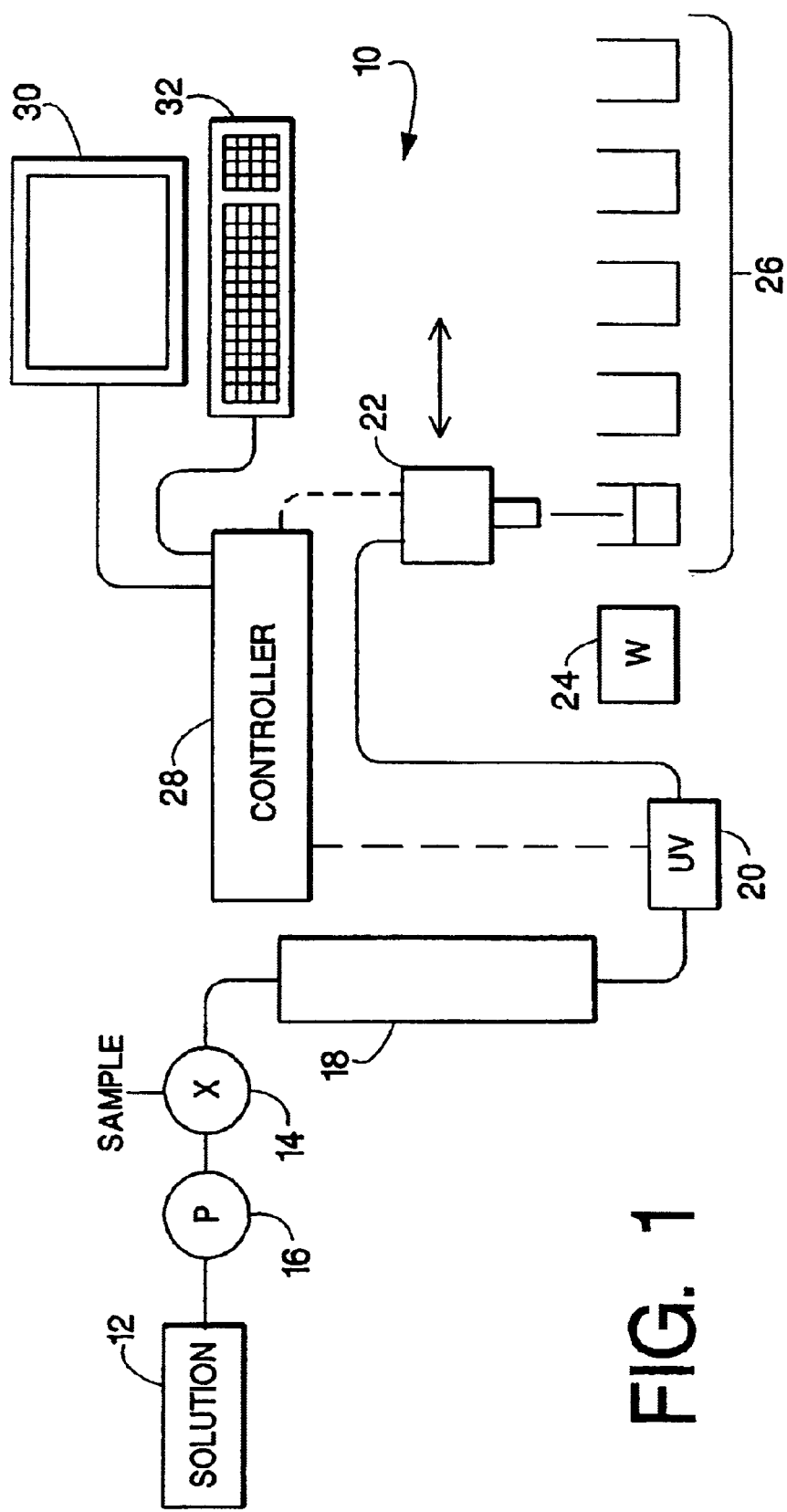
FIG. 1 is a block diagram of an automatic chromatography system.

Referring to FIG. 1, there is shown chromatography system 10 including source of solution 12, sample introduction port 14, pump 16, chromatography column 18, flow-through UV detector 20, fraction collection system 22, waste 24, fraction collection wells 26, controller 28 (e.g., a personal computer), monitor 30, and keyboard user input 32.

In operation, a solution 12, including a sample introduced therein at port 14, is pumped by pump 16 through chromatography column 18. The different compounds in the sample are delayed in passage through the column 18 to different extents and exit the column at different times. The solution, with the sample compounds therein at least partially separated from each other, passes through UV detector 20, which provides a signal indicating the absorbance of UV light by the solution passing therethrough to controller 28. The solution then continues to fraction collection system 22. Controller 28 controls fraction collection system 22 to direct the solution to waste 24 or a well 26 and to move from one well 26 to another, based upon the UV absorbance signals from UV detector 20. Controller 28 takes as inputs the UV absorbance signals at one or two times per second. Other data rates can be used.

Figure 2:
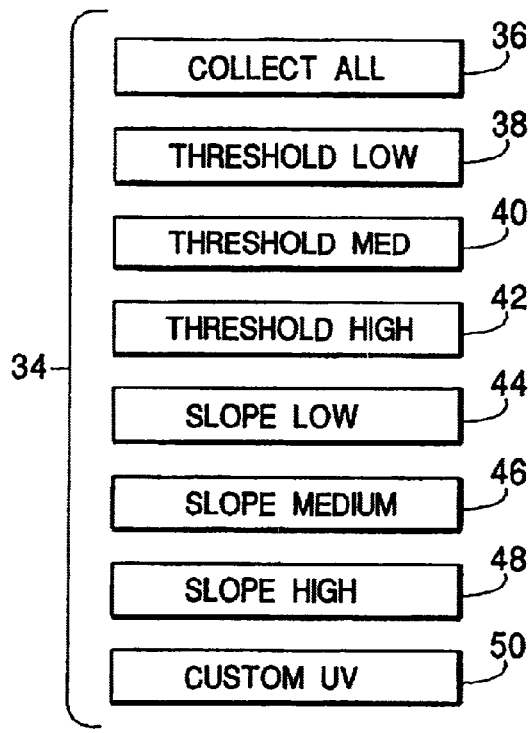
FIGS. 2–4 are representations of interactive screen displays on a monitor of the FIG. 1 system.

A user can specify the operation of the fraction collection system in response to the UV absorbance signals via a graphical interactive user interface provided by monitor 30 and keyboard 32. Referring to FIG. 2, there is shown menu 34, which is displayed on monitor 30. Menu 34 includes eight selection buttons 36–50 to permit the user to select the "collect all" mode with button 36, one of six automatic operation modes with buttons 38–48, or a custom user mode of operation with button 50. In the "collect all" mode, fraction collection system 22 continuously collects all solution from cartridge 18 and moves from one collection well 26 to another based upon the volume discharged.

In the threshold low, threshold medium or threshold high modes, selected by buttons 38, 40 and 42, the fraction collection system 22 begins directing solution from cartridge 18 to a collection well 26 after controller 28 determines that the UV signal from detector 20 has gone above a UV absorbance value threshold $T_v$ and will continue to discharge the solution to a collection well 26 as long as the sensed UV absorbance remains above $T_v$. In these modes the fraction collection system 22 also moves from one collection well 26 to another based upon the volume discharged. In the three modes, the values for $T_v$ are different, with the lowest being in the threshold low mode and the highest being in the threshold high mode. These modes of operation are considered value-based collection, because collection is based on the absorbance value. When the solution is not being directed to the wells 26 for collection, it is instead directed to waste 24.

The threshold low button 38, the threshold medium button 40, and the threshold high button 42 can be replaced by a single threshold button and box (not shown) in which the use could enter the desired threshold value.

In the slope low, slope medium or slope high modes, selected by buttons 44, 46 and 48, the fraction collection system 22 begins directing solution from cartridge 18 to a collection well 26 after controller 28 determines that two conditions have been met: (1) the UV signal from detector 20 has gone above a slope enable threshold $T_s$, and (2) the slope of the UV signal from detector 20 (i.e., the change in the absorbance value from one reading at the detector to the next) has gone above a slope threshold S. Fraction collection system 22 will continue to discharge the solution to a collection well 26 as long as the sensed UV absorbance remains above $T_s$, and the slope remains above S. In these modes the fraction collection system also moves from one collection well 26 to another based upon the volume discharged. In the various modes, the values for S are different, with the lowest being in the slope low mode and the highest being in the slope high mode. These modes of operation are considered slope-based collection, because collection is based on the rate of change of the absorbance values. When the solution is not being directed to the wells 26 for collection it is instead directed to waste 24.

Figure 4:
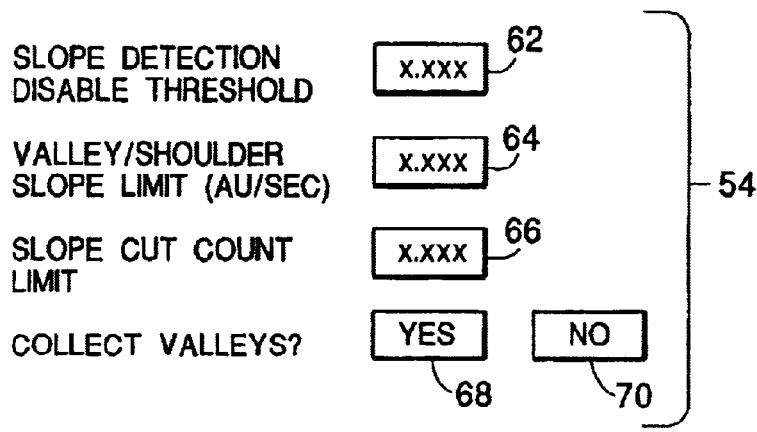
Figure 5:
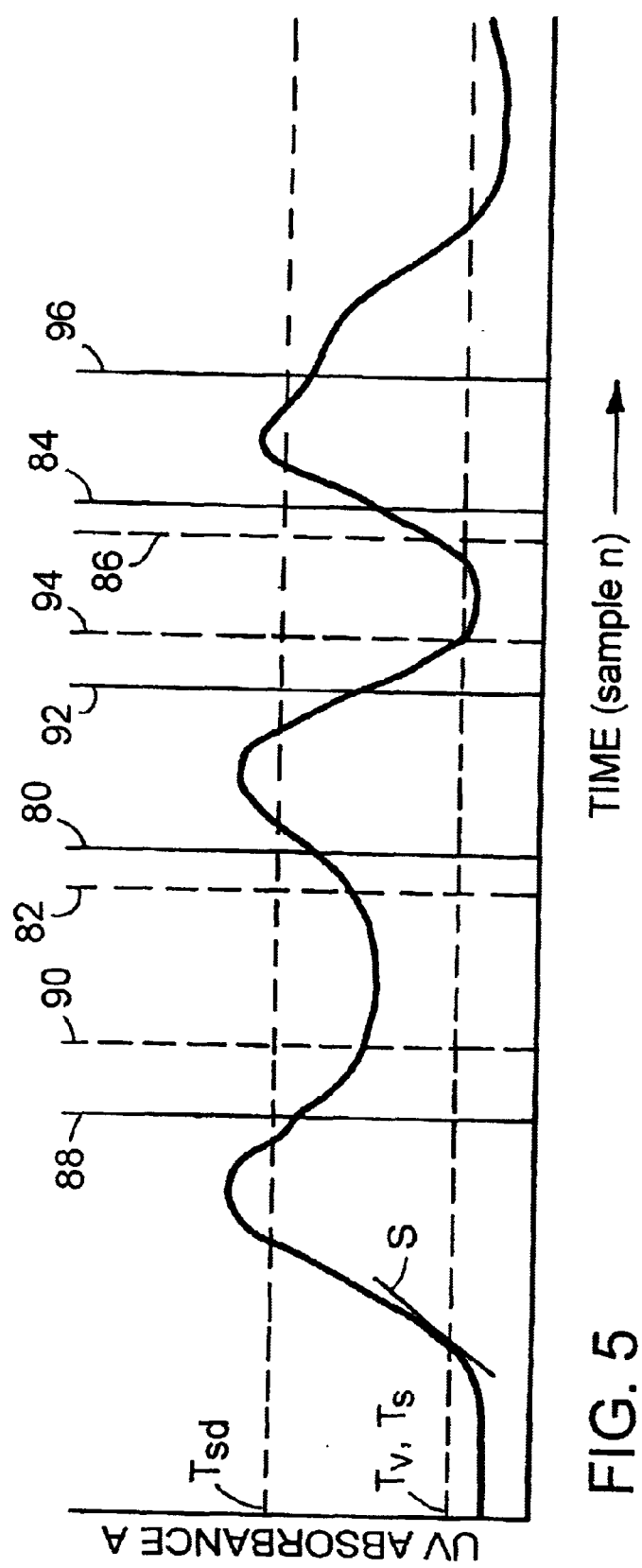
FIG. 5 is a graph of UV absorbance versus time illustrating various conditions for initiating and terminating collection and for making a fraction cut based upon the values of UV absorbance, the slope of UV absorbance over time, and the change in slope of UV absorbance over time.

In the custom UV mode, selected by button 50, the user can adjust the decisions for starting and stopping collection and for making cuts between collection wells based upon the detected UV absorbance. Selecting button 50 causes display screen 52 shown in FIG. 3, and completion of screen 52 causes display of screen 54 shown in FIG. 4. FIG. 5 is a graph of UV absorbance A[n] versus time, where A is UV absorbance, and time is in units of datapoint number n. In screens 52 and 54 the user selects values for various parameters, many of which are shown on FIG. 5, and enters the values into respective boxes 56–66. These include box 56 for value threshold $T_v$, box 58 for slope threshold S, box 60 for slope enable threshold $T_s$, box 62 for slope detection disable threshold $T_{sd}$, box 64 for valley threshold slope limit $T_{sl}$, and box 66 for slope cut count limit $C_c$. The user also selects either button 68 or button 70 to specify whether or not samples should be collected during valleys in the UV absorbance data. The set points for these parameters and collection conditions entered by the user are summarized in the following table.

| Set points (Symbol) | Explanation |
| --- | --- |
| 1. Value Threshold ($T_v$) | This is the value level minimum for value-based collection |
| 2. Slope Threshold (S) | This is the threshold slope that starts slope-based collection. |
| 3. Slope Enable Threshold ($T_s$) | This is the value level minimum to consider slope-based collection |
| 4. Slope Detection Disable Threshold ($T_{sd}$) | The threshold value for valley and shoulder collection. Above this value valleys and shoulders are ignored; below they are considered and cut. |
| 5. ValleyThreshold SlopeLimit ($T_{sL}$) | This is the slope trigger value for valley and shoulder collection, typically much smaller than S. |
| 6. SlopeCutCountLimit ($C_c$) | This adjusts sensitivity to turning off valley collection, with higher values resulting in higher fractions of the valleys being collected |
| Collection Conditionals | |
| 7. ValleySlope | These are Boolean values for slope-based and threshold collection modes indicating whether to collect valleys in fractions or to send them to waste. |
| 8. ValleyThreshold | |

The conditions for starting collection, making a fraction cut (move from one well 26 to another), and ending collection are set forth below.

Further Definitions

Value of the absorbance at time n is A[n],
where n is the sample (i.e., datapoint) number.
Change in absorbance, slope, is dA[n] = A[n] − A[n − 1].
Time (sample number) at which downward shoulder cut was made in $n_{ds}$.
K is the time delay in number of samples.
Starting conditions for fraction collection Slope collection mode: dA[n] > S and A[n] > $T_s$.
Value collection mode: A[n] > $T_v$.

-continued

Fraction cutting conditions during fraction collection

Upward shoulder cut: cut at time n + k, when A[n + k] < $T_{sd}$ and
dA[n] > 0 and dA[n] < $T_{s1}$ and dA[n + k] > 2 * $T_{s1}$.
Downward shoulder cut: cut at time n, when A[n] < $T_{sd}$ and
dA[n] < 0 and dA[n] > −$T_{s1}$.
Valley Cut: cut at time n, when dA[$n_{ds}$] < 0 and
dA[$n_{ds}$] > −$T_{s1}$ and dA[n] > 0, n − $n_{ds}$ > $C_c$.
Stopping conditions for fraction collection Slope collection mode: Stop at n: (1) if A[n] > $T_{sd}$ or
(2) if valley slope is false and dA[$n_{ds}$] < 0 and
dA[$n_{ds}$] > −$T_{s1}$ and dA[n] > 0 and n − $n_{ds}$ > $C_c$.
Value collection mode: Stop at n: (1) if A[n] < Tv or
(2) if valley slope is false and dA[$n_{ds}$] < 0 and
dA[$n_{ds}$] > −$T_{s1}$ and dA[n] > 0 and n − $n_{ds}$ > $C_c$.

These conditions will be described with reference to FIG. 5.

Value Collection Mode

Figure 3:
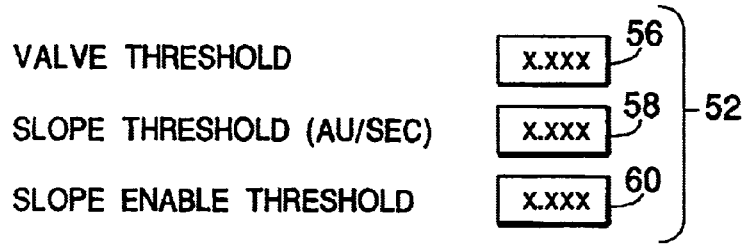

If a user wishes to operate in a value collection mode, he will set $T_v$ to the desired set point in box 56 (FIG. 3). Fraction collection system 22 will waste the solution while the absorbance value A[n] is below $T_v$ and will direct the solution to a collection well 26 while A[n] is greater than $T_v$. Thus, as indicated in the "starting condition for fraction collection" table above, collection will start when A[n]>$T_v$. Thereafter, collection system 22 will automatically advance from well 26 to another well 26 after a specified volume has been discharged into a well 26. If desired, the user can also specify fraction cutting based upon slopes when the slope values indicate the existence of different compounds. To do this the user must enter values for $T_{sd}$ in box 62, $T_{sl}$ in box 64, and $C_c$ in box 66 (FIG. 4).

An upward shoulder cut (e.g., as indicated by vertical lines 80, 82, 84, and 86 on FIG. 5) will be made at an inflection point on the curve that indicates the presence of an overlapping compound. As described in the "fraction cutting conditions" table above, the upward shoulder cut is made at time n+k, when the specified conditions are met. First, the aborbance value A[n] must be less than $T_{sd}$, because above this value slopes are not considered in order to avoid a false determination of noise at the top of a peak as a change in compound. Second, the slope dA[n] must be positive, indicating an upward portion of the curve. Third, the slope at time n must be less than $T_{sl}$, the trigger value, and fourth, the slope at time n+k must be greater than two times $T_{sl}$, in order to have a sufficient change in slope to indicate a different compound. Other multipliers could be used besides two. For example, the value could be another value greater than 1.0, e.g., a value between 1.5 and 2.5. The solid vertical lines 80, 84 indicate upward shoulder cuts that were made with $T_{sl}$, set to a higher slope threshold than for the cuts indicated at dashed vertical lines 82, 86.

A downward shoulder cut (e.g., as indicated by vertical lines 88, 90, 92, 94, and 96 on FIG. 5) will also be made at an inflection point on the curve that indicates the presence of an overlapping compound. As described in the "fraction cutting conditions" table above, the downward shoulder cut is made at time n, when the specified conditions are met. First, the absorbance value A[n] must be less than $T_{sd}$, because above this value slopes are not considered to avoid a false determination of noise at the top of a peak as a change in compound. Second, the slope dA[n] must be negative, indicating a downward portion of the curve. Third the slope at time n must be greater than —$T_{sl}$, the trigger value. Downward cuts are made as soon as the —$T_{sl}$ trigger is passed, without the need to consider slopes at different sample times. The solid vertical lines 88, 92 and 96 indicate downward shoulder cuts that were made with $T_{sl}$, set to a higher slope threshold than for the cuts indicated at dashed vertical lines 90, 94.

A "valley cut" can be made at a specified time after a downward shoulder cut has been made at time $n_{ds}$ (e.g., at time 90 on FIG. 5, assuming that a lower $T_{sl}$ value has been selected). The user sets the time for the valley cut by entering the value for $C_c$ into box 66 (FIG. 4). As described in the "fraction cutting conditions" table above, the valley cut is made at time n+1, when the specified conditions are met. The first two relate to the conditions indicating that a downward shoulder cut had been made at time rids, namely the slope at $n_{ds}$ was negative but greater than —$T_{sl}$. The next condition requires that the slope is positive at time n, i.e., that there is a valley between time $n_{ds}$ and time n. The last condition requires that the specified time, $C_c$, has passed since the downward shoulder trigger.

For further fraction collections to be made in a valley, the valley collection "YES" button 68 (FIG. 4) must be selected. If not, collection will stop pursuant to condition (2) indicated in the "stopping conditions for fraction collection" table above. These conditions are the same as for making a valley cut, and indicate stopping collection (i.e., directing to waste 24) at that time.

The other condition (condition (1) in the "stopping conditions for fraction collection" table above) that will cause stopping of fraction collection in the value collection mode is that the absorbance value A[n] goes below $T_v$.

Slope Collection Mode

If a user wishes to operate in a slope collection mode, he will set S and $T_s$, to the desired set points in boxes 56 and 60 (FIG. 3). Fraction collection system 22 will waste the solution until two conditions have been met, as indicated in the "starting condition for fraction collection" table above. First, the absorbance value A[n] must be greater than $T_s$. Second, the slope dA[n] must be greater than S. After these conditions have been met, controller 28 causes fraction collection system 22 to direct the solution to a collection well 26. After starting collection, collection system 22 will automatically advance from one well 26 to another well 26 after a specified volume has been discharged into a well 26.

If desired, the user can also specify fraction cutting based upon slopes when the changes in slope values indicate the existence of different compounds. The fraction cutting in the slope collection mode is the same as has already been described for the value collection mode. Thus the conditions in the "fraction cutting conditions" table apply in the slope collection mode as well.

The two situations for stopping collection in the slope collection mode are set forth in the "stopping conditions for fraction collection" table above. The first situation is when the absorbance value A[n] goes below the slope enable threshold $T_s$. The second is the same as the conditions for making a valley cut, as described above.

By using real-time analysis of the UV absorbance data, the system enables separation of fractions accurately and automatically. The detection based on UV slope and changes in UV slope allows for more fine tuned control of the fractionation process, leading to higher purity in the compounds collected and higher efficiencies. This is particularly useful when separating a mixture of unknown compounds, such that the operator cannot select optimal solvents and absorption characteristics ahead of time.

Other embodiments of the invention are within the scope of the appended claims.

What is claimed is:

1. A chromatography system for automatically separating different compounds in a sample by chromatography, and collecting fractions of said different compounds of said sample in separate fraction wells, said system comprising a chromatography column connected to receive a sample and separate different compounds in said sample, a detector connected to receive said sample from said column and outputting a signal indicating the presence of compounds in said sample passing through said detector, a fraction collector connected to receive said sample from said detector for directing fractions of said sample to separate fraction wells, and an electronic controller receiving inputs from said detector and controlling said fraction collector, said electronic controller monitoring said signal from said detector over time and initiating a cut from one well to another at said fraction collector when said signal over time experiences a shoulder where the slope of said signal over time does not change in sign but does change by more than a predetermined amount and is negative.

2. The system of claim 1 wherein said electronic controller determines to initiate a cut from one well to another at said fraction collector when said slope is negative and the slope is greater than a negative slope threshold.

3. The system of claim 2 wherein the slope must be less than a slope detection disable threshold in order for said controller to initiate said cut.

4. The system of claim 2 wherein said controller determines if said signal is in a valley by said slope being positive at a set time delay past said cut when said slope is negative.

5. The system of claim 4 where said controller causes said fraction collector to move to a new well after said set time delay.

6. The system of claim 5 further comprising a user interactive display and input device that permits said user to enter said set time delay.

7. The system of claim 4 where said controller ends collection after said set time delay.

8. The system of claim 4 further comprising a user interactive display and input device that permits said user to select whether to collect in valleys.

9. The system of claim 4 further comprising a user interactive display and input device that permits said user to enter said set time delay.

10. The system of claim 2 further comprising a user interactive display and input device that permits said user to enter said slope threshold disable detection threshold in order for said controller to initiate said cut.

11. A chromatography system for automatically separating different compounds in a sample by chromatography, and collecting fractions of said different compounds of said sample in separate fraction wells, said system comprising a chromatography column connected to receive a sample and separate different compounds in said sample, a detector connected to receive said sample from said column and outputting a signal indicating the presence of compounds in said sample passing through said detector, a fraction collector connected to receive said sample from said detector for directing fractions of said sample to separate fraction wells, and an electronic controller receiving inputs from said detector and controlling said fraction collector, said electronic controller monitoring said signal from said detector over time and initiating a cut from one well to another at said fraction collector when said signal over time experiences a shoulder where the slope of said signal over time does not change in sign but does change by more than a predetermined amount, wherein said electronic controller determines to initiate a cut from one well to another when said slope is positive, and the slope at one point in time is less than the slope threshold, and the slope at a later time is greater than X times the slope threshold, where X is greater than one.

12. The system of claim 11, where X is greater than 1.5.

13. The system of claim 12, wherein X is between 1.5 and 2.5.

14. The system of claim 12 wherein the slope at said later time must be less than a slope disable detection threshold in order for said controller to initiate cut.

15. The system of claim 14 further comprising a user interactive display and input device that permits said user to enter said slope disable detection threshold.

16. The system of claim 11 further comprising a user interactive display and input device that permits said user to enter said slope threshold.

17. The system of claim 10 or 11 further comprising a user interactive display and input device that permits said user to enter a threshold value for said signal for said controller to initiate and stop collection.

18. A chromatography system for automatically separating different compounds in a sample by chromatography, and collecting fractions of said different compounds of said sample in separate fraction wells, said system comprising a chromatography column connected to receive a sample and separate different compounds in said sample, a flow-through detector connected to receive said sample from said column and outputting a signal indicating the presence of compounds in said sample passing through said detector, a fraction collector connected to receive said sample from said detector for directing fractions of said sample to separate fraction wells, and an electronic controller receiving inputs from said detector and controlling said fraction collector, said electronic controller monitoring said signal from said detector over time and initiating a cut from one well to another at said fraction collector when said signal is less than a slope detection disable threshold and said signal over time experiences a specified change in slope condition.

19. The system of claim 18 wherein said change in slope condition is a change in a negative slope from one negative slope value that is less than a negative slope threshold to another negative slope value that is greater than said negative slope threshold.

20. The system of claim 18 wherein said change in slope condition is a change in a positive slope from one positive slope value that is less than a positive slope threshold to another positive slope value that is greater than said positive slope threshold.

* * * * *